(12) United States Patent
Ignagni et al.

(10) Patent No.: US 9,079,016 B2
(45) Date of Patent: Jul. 14, 2015

(54) REMOVABLE INTRAMUSCULAR ELECTRODE

(75) Inventors: Anthony R. Ignagni, Oberlin, OH (US); Raymond P. Onders, Shaker Heights, OH (US); James E. Gelbke, North Royalton, OH (US); Timothy Crish, Strongsville, OH (US)

(73) Assignee: Synapse Biomedical, Inc., Oberlin, OH (US)

( * ) Notice: Subject to any disclaimer, the term of this patent is extended or adjusted under 35 U.S.C. 154(b) by 2068 days.

(21) Appl. No.: 12/026,428

(22) Filed: Feb. 5, 2008

(65) Prior Publication Data

US 2008/0188867 A1    Aug. 7, 2008

Related U.S. Application Data

(60) Provisional application No. 60/899,799, filed on Feb. 5, 2007.

(51) Int. Cl.
*A61B 19/00* (2006.01)
*A61N 1/05* (2006.01)

(52) U.S. Cl.
CPC ................................ *A61N 1/0502* (2013.01)

(58) Field of Classification Search
CPC ... A61N 1/0502; A61N 1/0472; A61N 1/048; A61N 1/0488; A61N 1/0558
USPC ......................................................... 606/129
See application file for complete search history.

(56) References Cited

U.S. PATENT DOCUMENTS

| 1,693,734 A | 12/1928 | Waggoner |
| 2,532,788 A | 12/1950 | Sarnoff |

(Continued)

FOREIGN PATENT DOCUMENTS

| EP | 996482 A1 | 5/2000 |
| EP | 873155 B1 | 6/2003 |

(Continued)

OTHER PUBLICATIONS

Ayas et al; Prevention of human diaphragm atrophy with short periods of electrical stimulation; Am J Respir Crit Care Med; vol. 159; pp. 2018-2020; 1999.

(Continued)

*Primary Examiner* — Victor Nguyen
*Assistant Examiner* — Kevin Everage
(74) *Attorney, Agent, or Firm* — Shay Glenn LLP

(57) ABSTRACT

An implantable medical electrode system for intramuscular use that is readily removable is provided, as well as methods for its use. The system includes an electrode, an electrical lead mechanically and electrically connected to the electrode and extending proximally, and a tether bonded to the electrode and extending proximally. A conductor with an insulated portion enwraps the electrical lead; an uninsulated portion enwraps the electrode. Some embodiments may include a tissue-piercing guide such as a needle. In some embodiments, the electrode includes a barb, although in some of these embodiments the tether does not extend through the barb. The method of using the system includes inserting the through a target tissue, pulling the electrode with the needle into the target tissue, and extending the electrical lead and tether proximally to an electrical connection. Methods are further provided for removing the electrode which take advantage of structural features of the system.

6 Claims, 1 Drawing Sheet

(56) References Cited

U.S. PATENT DOCUMENTS

| | | | |
|---|---|---|---|
| 2,664,880 A | 1/1954 | Wales, Jr. | |
| 4,699,875 A | 10/1987 | Appel | |
| 4,773,393 A | 9/1988 | Haber et al. | |
| 4,827,935 A | 5/1989 | Geddes et al. | |
| 4,830,008 A | 5/1989 | Meer | |
| 4,863,438 A | 9/1989 | Gauderer et al. | |
| 4,989,617 A | 2/1991 | Memberg et al. | |
| 5,056,519 A | 10/1991 | Vince | |
| 5,074,846 A | 12/1991 | Clegg et al. | |
| 5,146,918 A | 9/1992 | Kallok et al. | |
| 5,314,463 A | 5/1994 | Camps et al. | |
| 5,335,657 A | 8/1994 | Terry et al. | |
| 5,368,035 A | 11/1994 | Hamm et al. | |
| 5,429,636 A | 7/1995 | Shikhman et al. | |
| 5,472,438 A | 12/1995 | Schmit et al. | |
| 5,483,969 A | 1/1996 | Testerman et al. | |
| 5,524,632 A | 6/1996 | Stein et al. | |
| 5,527,358 A | 6/1996 | Mehmanesh et al. | |
| 5,678,535 A | 10/1997 | DiMarco | |
| 5,716,392 A | 2/1998 | Bourgeois et al. | |
| 5,718,248 A | 2/1998 | Trumble et al. | |
| 5,792,165 A | 8/1998 | Klieman et al. | |
| 5,797,923 A | 8/1998 | Aiyar et al. | |
| 5,813,399 A | 9/1998 | Isaza et al. | |
| 5,814,086 A | 9/1998 | Hirschberg et al. | |
| 5,849,290 A | 12/1998 | Brown et al. | |
| 5,851,783 A | 12/1998 | Appel et al. | |
| 6,035,856 A | 3/2000 | LaFontaine et al. | |
| 6,194,217 B1 | 2/2001 | Matson | |
| 6,198,970 B1 | 3/2001 | Freed et al. | |
| 6,210,970 B1 | 4/2001 | Matson | |
| 6,245,053 B1 | 6/2001 | Benjamin | |
| 6,254,425 B1* | 7/2001 | Shchervinsky et al. | 439/502 |
| 6,311,692 B1 | 11/2001 | Vaska et al. | |
| 6,321,109 B2 | 11/2001 | Ben-Haim et al. | |
| 6,360,740 B1 | 3/2002 | Ward et al. | |
| 6,397,108 B1 | 5/2002 | Camps et al. | |
| 6,405,732 B1 | 6/2002 | Edwards et al. | |
| 6,415,183 B1 | 7/2002 | Scheiner et al. | |
| 6,463,327 B1 | 10/2002 | Lurie et al. | |
| 6,477,423 B1 | 11/2002 | Jenkins | |
| 6,571,127 B1 | 5/2003 | Ben-Haim et al. | |
| 6,645,145 B1 | 11/2003 | Dreschel et al. | |
| 6,845,271 B2 | 1/2005 | Fang et al. | |
| 6,918,871 B2 | 7/2005 | Schulze | |
| 6,947,792 B2 | 9/2005 | Ben-Haim et al. | |
| 7,006,871 B1 | 2/2006 | Darvish et al. | |
| 7,044,921 B2 | 5/2006 | Asmus et al. | |
| 7,071,194 B2 | 7/2006 | Teng | |
| 7,107,092 B2 | 9/2006 | Goldstein et al. | |
| 7,120,497 B2 | 10/2006 | Ben-Haim et al. | |
| 7,155,278 B2 | 12/2006 | King et al. | |
| 7,165,551 B2 | 1/2007 | Edwards et al. | |
| 7,195,881 B2 | 3/2007 | Geffard | |
| 7,206,636 B1 | 4/2007 | Turcott | |
| 7,207,946 B2 | 4/2007 | Sirokman | |
| 7,221,978 B2 | 5/2007 | Ben-Haim et al. | |
| 7,225,016 B1 | 5/2007 | Koh | |
| 7,329,489 B2 | 2/2008 | Kaddurah-Daouk et al. | |
| 7,356,521 B2 | 4/2008 | Wang et al. | |
| 7,418,298 B2 | 8/2008 | Shiroff et al. | |
| 8,706,236 B2 | 4/2014 | Ignagni et al. | |
| 2001/0025177 A1 | 9/2001 | Woloszko et al. | |
| 2001/0049497 A1 | 12/2001 | Kalloo et al. | |
| 2002/0103424 A1 | 8/2002 | Swoyer et al. | |
| 2003/0040785 A1 | 2/2003 | Maschino et al. | |
| 2003/0148404 A1 | 8/2003 | Michaelson | |
| 2003/0171672 A1 | 9/2003 | Varghese et al. | |
| 2003/0175832 A1 | 9/2003 | Marton et al. | |
| 2003/0195600 A1 | 10/2003 | Tronnes et al. | |
| 2004/0003813 A1 | 1/2004 | Banner et al. | |
| 2004/0044377 A1 | 3/2004 | Larsson | |
| 2004/0064069 A1 | 4/2004 | Reynolds et al. | |
| 2004/0122360 A1 | 6/2004 | Waldhauser et al. | |
| 2004/0127954 A1 | 7/2004 | McDonald | |
| 2004/0167437 A1 | 8/2004 | Sharrow et al. | |
| 2004/0167442 A1 | 8/2004 | Shireman et al. | |
| 2004/0167443 A1 | 8/2004 | Shireman et al. | |
| 2004/0172090 A1 | 9/2004 | Janzig et al. | |
| 2004/0177388 A1 | 9/2004 | Botas et al. | |
| 2004/0254572 A1 | 12/2004 | McIntyre et al. | |
| 2004/0260198 A1 | 12/2004 | Rothberg et al. | |
| 2004/0260245 A1 | 12/2004 | Clem et al. | |
| 2004/0260246 A1 | 12/2004 | Desmond | |
| 2004/0260337 A1 | 12/2004 | Freed | |
| 2005/0021102 A1* | 1/2005 | Ignagni et al. | 607/42 |
| 2005/0033394 A1 | 2/2005 | Seifert et al. | |
| 2005/0042589 A1 | 2/2005 | Hatlestad et al. | |
| 2005/0049523 A1 | 3/2005 | Crank | |
| 2005/0054950 A1 | 3/2005 | Parins | |
| 2005/0054951 A1 | 3/2005 | Parins | |
| 2005/0054952 A1 | 3/2005 | Eskuri et al. | |
| 2005/0080463 A1 | 4/2005 | Stahmann et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0107781 A1 | 5/2005 | Ostrovsky et al. | |
| 2005/0107812 A1 | 5/2005 | Starksen et al. | |
| 2005/0107860 A1 | 5/2005 | Ignagni et al. | |
| 2005/0109340 A1 | 5/2005 | Tehrani | |
| 2005/0113710 A1 | 5/2005 | Stahmann et al. | |
| 2005/0115561 A1 | 6/2005 | Stahmann et al. | |
| 2005/0124917 A1 | 6/2005 | Skujins et al. | |
| 2005/0137501 A1 | 6/2005 | Euteneuer et al. | |
| 2005/0148026 A1 | 7/2005 | Bowser et al. | |
| 2005/0148818 A1 | 7/2005 | Mesallum | |
| 2005/0165457 A1 | 7/2005 | Benser et al. | |
| 2005/0209653 A1 | 9/2005 | Herbert et al. | |
| 2005/0240241 A1 | 10/2005 | Yun et al. | |
| 2005/0277945 A1 | 12/2005 | Saadat et al. | |
| 2006/0030894 A1 | 2/2006 | Tehrani | |
| 2006/0035849 A1 | 2/2006 | Spiegelman et al. | |
| 2006/0036294 A1 | 2/2006 | Tehrani | |
| 2006/0041022 A1 | 2/2006 | Pasinetti | |
| 2006/0068452 A1 | 3/2006 | Goldknopf et al. | |
| 2006/0088862 A1 | 4/2006 | Lee | |
| 2006/0115854 A1 | 6/2006 | Goldknopf et al. | |
| 2006/0115855 A1 | 6/2006 | Goldknopf et al. | |
| 2006/0115856 A1 | 6/2006 | Goldknopf et al. | |
| 2006/0115867 A1 | 6/2006 | Goldknopf et al. | |
| 2006/0121619 A1 | 6/2006 | Bowser | |
| 2006/0122662 A1 | 6/2006 | Tehrani et al. | |
| 2006/0130161 A1 | 6/2006 | Genain | |
| 2006/0130833 A1 | 6/2006 | Younes | |
| 2006/0142815 A1 | 6/2006 | Tehrani et al. | |
| 2006/0149316 A1 | 7/2006 | DeVries et al. | |
| 2006/0149334 A1 | 7/2006 | Tehrani et al. | |
| 2006/0155222 A1 | 7/2006 | Sherman et al. | |
| 2006/0155341 A1 | 7/2006 | Tehrani et al. | |
| 2006/0160087 A1 | 7/2006 | McGrath et al. | |
| 2006/0167523 A1 | 7/2006 | Tehrani et al. | |
| 2006/0200004 A1 | 9/2006 | Wilk | |
| 2006/0224209 A1 | 10/2006 | Meyer | |
| 2006/0237023 A1 | 10/2006 | Cox et al. | |
| 2006/0247729 A1 | 11/2006 | Tehrani et al. | |
| 2006/0258667 A1 | 11/2006 | Teng | |
| 2006/0281809 A1 | 12/2006 | Miller et al. | |
| 2006/0282131 A1 | 12/2006 | Caparso et al. | |
| 2006/0286167 A1 | 12/2006 | Staunton et al. | |
| 2006/0287679 A1 | 12/2006 | Stone | |
| 2007/0016172 A1 | 1/2007 | Charukhchian | |
| 2007/0017809 A1 | 1/2007 | Goldknopf et al. | |
| 2007/0021421 A1 | 1/2007 | Hampton | |
| 2007/0021500 A1 | 1/2007 | Twyman et al. | |
| 2007/0021795 A1 | 1/2007 | Tehrani | |
| 2007/0038127 A1 | 2/2007 | Goldstein et al. | |
| 2007/0049793 A1 | 3/2007 | Ignagni et al. | |
| 2007/0054852 A1 | 3/2007 | Lin et al. | |
| 2007/0072943 A1 | 3/2007 | Miller et al. | |
| 2007/0078099 A1 | 4/2007 | McLaurin | |
| 2007/0087000 A1 | 4/2007 | Walsh et al. | |

(56) References Cited

U.S. PATENT DOCUMENTS

| | | |
|---|---|---|
| 2007/0087314 A1 | 4/2007 | Gomo |
| 2007/0098812 A1 | 5/2007 | Feinstein et al. |
| 2007/0117772 A1 | 5/2007 | Bennett et al. |
| 2007/0118183 A1 | 5/2007 | Gelfand et al. |
| 2007/0122813 A1 | 5/2007 | Salomon et al. |
| 2007/0150006 A1 | 6/2007 | Libbus et al. |
| 2007/0150023 A1 | 6/2007 | Ignagni et al. |
| 2007/0172820 A1 | 7/2007 | Kaddurah-Daouk et al. |
| 2007/0191908 A1 | 8/2007 | Jacob et al. |
| 2007/0196780 A1 | 8/2007 | Ware et al. |
| 2007/0197932 A1 | 8/2007 | Feke et al. |
| 2007/0202515 A1 | 8/2007 | Hadlock et al. |
| 2007/0202537 A1 | 8/2007 | Lingappa et al. |
| 2007/0221224 A1 | 9/2007 | Pittman et al. |
| 2007/0225261 A1 | 9/2007 | Miller et al. |
| 2007/0240718 A1 | 10/2007 | Daly |
| 2007/0250162 A1 | 10/2007 | Royalty |
| 2007/0265611 A1 | 11/2007 | Ignagni et al. |
| 2007/0274992 A1 | 11/2007 | Michalovich et al. |
| 2007/0282388 A1 | 12/2007 | Sandyk |
| 2007/0292403 A1 | 12/2007 | Nivaggioli |
| 2007/0292410 A1 | 12/2007 | Cashman et al. |
| 2007/0298998 A1 | 12/2007 | Paige et al. |
| 2008/0003208 A1 | 1/2008 | Nivaggioli |
| 2008/0121231 A1 | 5/2008 | Sinderby et al. |
| 2011/0060381 A1 | 3/2011 | Ignagni et al. |
| 2013/0238053 A1 | 9/2013 | Ignagni et al. |

FOREIGN PATENT DOCUMENTS

| | | |
|---|---|---|
| EP | 1634617 A1 | 3/2006 |
| EP | 1653863 A2 | 5/2006 |
| EP | 1658020 A1 | 5/2006 |
| EP | 1660177 A1 | 5/2006 |
| EP | 1663370 A2 | 6/2006 |
| EP | 1667757 A2 | 6/2006 |
| EP | 1670611 A2 | 6/2006 |
| EP | 1684655 A2 | 8/2006 |
| EP | 1393773 B1 | 10/2006 |
| EP | 1306104 B1 | 1/2007 |
| EP | 1205202 B1 | 6/2007 |
| WO | WO 86/00234 A1 | 1/1986 |
| WO | WO 2005/039691 A1 | 5/2005 |
| WO | WO2005/044079 A2 | 5/2005 |
| WO | WO 2006/062710 A1 | 6/2006 |
| WO | WO 2006/079152 A1 | 8/2006 |
| WO | WO 2006/083675 A2 | 8/2006 |
| WO | WO 2006/088696 A2 | 8/2006 |
| WO | WO 2006/121447 A2 | 11/2006 |
| WO | WO 2006/124023 A1 | 11/2006 |
| WO | WO 2006/131150 A1 | 12/2006 |
| WO | WO 2006/138069 A1 | 12/2006 |
| WO | WO 2007/035804 A2 | 3/2007 |
| WO | WO 2007/053230 A2 | 5/2007 |
| WO | WO 2007/058780 A2 | 5/2007 |
| WO | WO 2007/058938 A2 | 5/2007 |
| WO | WO 2007/061902 A2 | 5/2007 |
| WO | WO 2007/082384 A1 | 7/2007 |
| WO | WO 2007/103585 A2 | 9/2007 |
| WO | WO 2007/109443 A2 | 9/2007 |
| WO | WO 2007/128002 A2 | 11/2007 |

OTHER PUBLICATIONS

Bhadra et al.; Extraction force and tissue change during removal of a tined intramuscular electrode from rat gastrocnemius; Annals of Biomedical Engineering; vol. 34; No. 6; pp. 1042-1050; Jun. 2006.

DiMarco et al.; Phrenic nerve pacing in a tetraplegic patient via intramuscular diaphragm electrodes; American Journal of Respiratory and Critical Care Medicine; vol. 166 (12 Pt 1); pp. 1604-1606; Dec. 15, 2002.

DiMarco A. F.; Restoration of respiratory muscle function following spinal cord injury—Review of electrical and magnetic stimulation techniques; Respiratory Physiology & Neurobiology; 147; 273-287; 2005.

Knutson et al.; Electrode fracture rates and occurrences of infection and granuloma associated with percutaneous intramuscular electrodes in upper-limb functional electrical stimulation applications; Journal of Rehabilitation Research and Development; vol. 39; No. 6; pp. 671-684, Nov./Dec. 2002.

Nochomovitz et al.; Conditioning of the diaphragm with phrenic nerve stimulation after prolonged disuse; American Review of Respiratory Disease; vol. 130; No. 4; 325-329; Oct. 1984.

Nochomovitz et al.; Diaphragm activation with intramuscular stimulation in dogs; American Review of Respiratory Disease; vol. 127; No. 3; 685-687; Mar. 1983.

Onders et al.; Early results of laparoscopic motor point diaphragm pacing in amyotrophic lateral sclerosis; Amyotrophic Lateral Sclerosis (Abstracts from the 16th Intl. Symp. ALS/MND; vol. 6, supp. 1; ISSN1743-4475; pp. 142-143; Dec. 2005.

Onders et al.; Mapping the phrenic nerve motor point: the key to a successful laparoscopic diaphragm pacing system in the first human series; Surgery; vol. 136; No. 4; 819-26; Oct. 2004.

Peterson et al.; Long-term intramuscular electrical activation of the phrenic nerve: Safety and reliability; IEEE; vol. 41; No. 12; pp. 1115-1126; Dec. 1994.

Peterson et al.; Electrical activation of respiratory muscles by methods other than phrenic nerve cuff electrodes; Pacing and Clinical Electrophysiology; vol. 12; No. 5; pp. 854-878; May 1989.

Peterson et al.; Intramuscular electrical activation of the phrenic nerve; IEEE Transactions on Biomedical Engineering; vol. BME-33; No. 3; 342-351; Mar. 1986.

Polkey et al.; Influence of acute lung volume change on contractile properties of human diaphragm; Journal of Applied Physiology; vol. 85, No. 4; pp. 1322-1328; Oct. 1998.

Sarnoff et al.; Electrophrenic respiration; Science; vol. 108; 482; Oct. 29, 1948.

Schmit, et al.; Laparoscopic placement of electrodes for diaphragm pacing using stimulation to locate the phrenic nerve motor points; IEEE Trans on Rehab Engineer; vol. 6; No. 4; 382-390; Dec. 1998.

Ignagni et al; U.S. Appl. No. 11/716,475 entitled "Ventilatory assist system and methods to improve respiratory function," filed Mar. 9, 2007.

Ignagni et al; U.S. Appl. No. 11/467,025 entitled "Method and apparatus for grasping an abdominal wall," filed Aug. 24, 2006.

Ignagni et al.; U.S. Appl. No. 12/690,410 entitled "Device and Method of Neuromodulation to Effect a Functionally Restorative Adaption of the Neuromuscular System," filed Jan. 20, 2010.

Kalloo et al.; Flexible transgastric peritoneoscopy: a novel approach to diagnosis and therapeutic intervention in the peritoneal cavity; Gastrointestinal Endoscopy; vol. 60; No. 1; pp. 114-117; 2004.

Ignagni et al.; U.S. Appl. No. 12/261,979 entitled "Method of improving sleep disordered breathing," filed Oct. 30, 2008.

Onders et al.; U.S. Appl. No. 12/122,482 entitled "Devices and methods for assessing motor point electromyogram as a biomarker," filed May 16, 2008.

DeCarvalho et al.; Motor neuron disease presenting with respiratory failure; Journal of the Neurological Sciences; vol. 139; No. Suppl.; 1996; pp. 117-122.

Stewart et al.; Electromyography of respiratory muscles in amyotrophic lateral sclerosis; Journal of the Neurological Sciences; vol. 191; No. 1-2; Oct. 15, 2001; pp. 67-73.

Zifko et al.; Central and peripheral respiratory electrophysiological studies in myotonic dystrophy; Brain; vol. 119; 1996; pp. 1911-1922.

de Carvalho et al.; Medical technology assessment: Electrodiagnosis in motor neuron diseases and amyotrophic lateral sclerosis; Neurophysiol. Clin.; Oct. 2001; 31 (5); pp. 341-348.

D'Honneur et al.; Comparison of the effects of mivacurium on the diaphragm and geniohyoid muscles; British Journal of Anesthesia; 77(6); pp. 716-719; Dec. 1996.

McGee et al.; A reliable method for monitoring intraabdominal pressure during natural orifice translumenal endoscopic surgery; Surg Endosc.; 21(4): pp. 672-676; Apr. 2007.

Onders, Raymond P.; The Utility of Flexible Endoscopy During Advanced Laparoscopy; Seminars in Laparoscopic Surgery; vol. 10, No. 1; pp. 43-48; Mar. 2003.

* cited by examiner

REMOVABLE INTRAMUSCULAR ELECTRODE

REFERENCE TO RELATED APPLICATIONS

This application claims priority under 35 U.S.C. §119 to U.S. Provisional Patent Application No. 60/899,799, filed on Feb. 5, 2007, the disclosure of which is incorporated by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The invention relates to intramuscular electrodes, such as diaphragm pacing electrodes.

BACKGROUND OF THE INVENTION

Intramuscular diaphragm pacing stimulation (DPS) has been shown to be a viable therapeutic technique for replacement of chronic mechanical ventilation in patients with respiratory insufficiency, such as high-level spinal cord injury. DPS has also been demonstrated to have a clinically relevant effect in conditioning the diaphragm of patients with amyotrophic lateral sclerosis. These therapeutic applications of electrodes are ones in which the electrode are typically designed to be implanted for duration of the life of the patient or until mechanical failure of the electrode. Therefore, the electrodes are typically constructed with significant redundancy, reinforcement, and barbing to promote longevity and stabilization in the target muscle.

Some intramuscular electrodes have been developed for shorter-term applications. For example, intramuscular, percutaneous, single-helix design electrodes have been used for functional electrical stimulation in applications where the electrode is placed through a percutaneous needle insertion into the target muscle. These electrodes are typically removed by pulling axially on the electrode lead. However, the barbs on the electrodes, as well as fibrosis and encapsulation of the electrode by the surrounding tissue, frequently resist or complicate removal of the electrodes. The electrodes and/or the wires extending proximally from them therefore frequently break during removal, thus leaving the electrode or a portion thereof in the muscle or subcutaneous tissue, as well as creating an undesirable level of tissue disturbance. See Peterson et al., "Long-Term Intramuscular Electrical Activation of the Phrenic Nerve: Safety and Reliability," *IEEE Trans Biomed. Eng.*, vol. 41, no. 12 pp. 1115-26 (December 1994).

A number of design features are desirable in intramuscular electrodes that have not yet been fully met by available products. Most basically, intramuscular electrodes need to meet the design criteria of being able to deliver the desired level of stimulus to target tissue, and be able to mechanically survive such use. If extraction of the electrode is necessary, it is an advantage for the electrode to survive extraction without breaking apart and generating "unretrieved device fragments" (UDFs). UDFs are a serious hazard; the FDA health notifications report about 1000 adverse events per year that are related to UDFs. Additionally, the extraction undesirably and almost inevitably visits at least some trauma upon the target tissue. Data have shown that extractions of simple intramuscular helical electrodes (Case Western Reserve University type) result in a fracture rate of 53% of electrodes with known status of integrity recorded (Knutson et al., "Electrode fracture rates and occurrences of infection and granuloma associated with percutaneous intramuscular electrodes in upper-limb functional electrical stimulation applications," *J. Rehab. Res. & Dev.*, vol. 39, no. 6, pp. 671-83 (November/December 2002)). See also Bhadra et al., "Extraction Force and Tissue Change During Removal of a Tined Intramuscular Electrode from Rat Gastrocnemius," *Ann. Biomed. Eng.*, vol. 34, no. 6, pp. 1042-50 (June 2006).

SUMMARY OF THE INVENTION

For percutaneous muscle stimulation of a temporary or short-term duration, it is desirable to use electrodes that can be easily removed without significant trauma to the muscle or other surrounding tissue and without leaving portions of the electrode behind. The present invention provides such electrodes and a method of using such electrodes. In some embodiments, the invention is a removable, percutaneous electrode that may be implanted into muscle tissue using laparoscopic, thorascopic, or open surgical techniques.

The invention relates to a medical electrode system that includes a removably-implantable electrode and methods of using the system, such methods being summarized below after first summarizing the system. The medical electrode system includes an electrode, an electrical lead mechanically and electrically connected to the electrode and extending proximally from the electrode, and an electrode tether bonded to the electrode and extending proximally from the electrode. In some embodiments, the medical electrode system may further include a tissue-piercing guide attached to the distal end of the electrode; and in some of these embodiments the tissue piercing guide may include a needle having a flared proximal end and a sharp distal end.

In some embodiments of the medical electrode system, the electrical lead surrounds at least a portion of the tether. The electrical lead of the system includes an insulated conductor, and the electrode includes an uninsulated portion of the conductor. The medical electrode system may further include an electrical connector attached to a proximal end of the electrical lead, and the electrical connector may be mechanically attached to the tether.

In some embodiments, the medical electrode system may further include a flexible barb. In some embodiments, the tether includes a core that extends through the electrical lead and the electrode; in some of these embodiments that core does not extend through the barb. In some embodiments of the system, the core is connected to the tissue-piecing guide.

In some embodiments of the medical electrode system the tissue-piercing guide comprises a needle, and in some of these embodiments, the needle may have a flared proximal end and a sharp distal end. In some embodiments of medical electrode system the core may include a distally terminal knob positioned distal to the electrode; the knob being configured to engage a delivery instrument to facilitate ejection of the electrode from the instrument.

With regard to the method aspect of the invention, a method of using an electrode in target tissue in a patient includes inserting a tissue-piercing guide into and through the target tissue, pulling an electrode connected to a proximal end of the tissue-piercing guide into the target tissue (the electrode being connected to the tissue-piercing guide by a tether extending distally from the electrode), and extending an electrical lead and the tether proximally from the electrode to an electrical connection location. In some embodiments of the method, the electrode includes a barb, and the method includes pulling the barb into the target tissue.

Method embodiments of using the electrode may further include cutting the tether between the electrode and the tissue-piercing guide after the pulling step, and removing the tissue-piercing guide from the patient. The method may also further include removing the electrode from the target tissue; the removing step may include pulling proximally on the electrical lead and pulling proximally on the tether. In some embodiments of the system, the electrical lead and the tether terminate in an electrical connector, and with these embodiments, the step of removing step may further include removing the electrical connector from the electrical lead and tether. In some embodiments of the system, the electrical lead surrounds at least a portion of the tether, and with these embodiments, the step of removing the electrode may further include separating the electrical lead and the tether prior to the pulling steps.

In another embodiment of a method for using the electrode system in a target tissue of a patient, the method includes inserting an electrode into the target tissue (the electrode being bonded to a tether and electrically connected to an electrical lead), and extending an electrical lead and the tether proximally from the electrode to an electrical connection location. In some embodiments, the method may further include removing the electrode from the target tissue, in which case the removing step includes pulling proximally on the electrical lead and pulling proximally on the tether. In some embodiments of the system, the electrical lead and tether terminate in an electrical connecter, and in such embodiments the removing step may further include removing the electrical connector from the electrical lead and tether. In some embodiments of the system, the electrical lead surrounds at least a portion of the tether, and in such embodiments, the removing step may further include separating the electrical lead and the tether prior to the pulling steps.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments in which the principles of the invention are utilized, and by reference to the accompanying drawings.

DETAILED DESCRIPTION OF THE INVENTION

Data have shown that forces necessary for extraction range from about 0.25N at time of implant to 6.0N after four weeks of implantation. More complex intramuscular helical electrodes (Peterson type) have shown long-term stability, a cumulative total exceeding 520 implant electrode-years, without fracture, but significantly more force is required to extract them. The extraction force for Peterson type electrodes range from 0.6N at time of implant to 5.8N after four weeks of implantation. The force required to pull apart the heavy barbing of a Peterson type electrode ranges from 4N-8N. There is a need for therapeutic electrodes that have the structural integrity to resist breakage during extraction, in order to minimize the generation of UDFs, and/or have design features that minimize the force required for their extraction.

Figure 1:
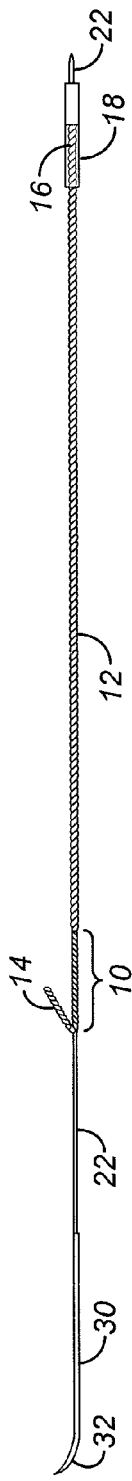
FIG. 1 is a side elevational view of an intramuscular electrode according to one embodiment of the invention.

FIG. 1 shows one embodiment of an electrode system of this invention, which includes electrode 10 and electrode lead 12 formed from a helically wound insulated conductor. In some other embodiments, two helically interwoven conductors form the lead and electrode. The insulation has been removed from the part of the conductor, thus forming electrode 10, while the insulation covering the lead portion 12 remains intact. Electrode 10 is bent back to form a barb 14 as shown. Electrode 10 and lead 12 terminate proximally in a connector 16 that may be connector to an exterior stimulator cable providing stimulation pulses through the lead to the electrode after the electrode has been implanted. As shown, connector 16 has a sleeve 18 covering the electrical connection between lead 12 and a connector pin 20. Sleeve 18 may also provide strain relief.

A tether, formed, for example, as a core 22, is disposed within the helix of lead 12 and electrode 10. The core 22 may be formed of a variety of materials, for example polypropylene suture material, absorbable suture material or any other suitable material. Core 22 being flexible, it imparts flexibility to the electrode as a whole. Core 22 is primarily attached or bonded to electrode 10, but the core's attachment may extend to or through the length of lead 12. Attachment of the core, at the site of electrode 10, may be performed by a mechanical heating that results in an infiltration and expansion of the core material into the electrode windings. This mechanical fixation results in a structural integrity that can withstand 10N of force to pull the core from the electrode, thus significantly reducing or eliminating the generation of unretrieved device fragments upon extraction. In the embodiments shown in FIGS. 1-3, the attachment between the core and the electrical lead is achieved by heating the core and electrode so that the polypropylene expands within the helix of electrode 10. In the embodiments shown in FIGS. 1-3, core 22 extends only through the portion of the electrode that is in line with lead 12 and does not extend into barb 14. In other embodiments, the core may extend throughout the entire electrode. The electrode may be attached to the core in other ways as well, such as by crimping. The proximal end of core 22 is attached to a connector 16, such as by crimping.

Figure 2:
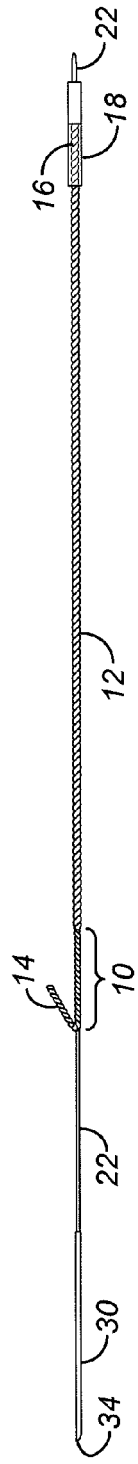
FIG. 2 is a side elevational view of an intramuscular electrode according to a second embodiment of the invention.
Figure 3:
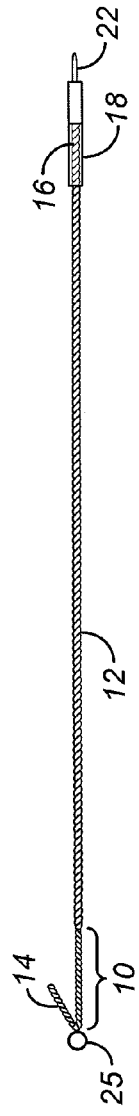
FIG. 3 is a side elevational view of an intramuscular electrode according to a third embodiment of the invention.

The electrode of this invention may be delivered and implanted into muscle tissue by any conventional means. The embodiments shown in FIGS. 1-3 depict an electrode implantation device that is integrated with the electrode and lead. As shown, core 22 extends through and past electrode 10 to a tissue-piercing guide, such as a needle 30. Needle 30 is attached to core 22 by crimping or by some other suitable means. As shown in FIG. 1, needle 30 has a curved tip 32 at its distal end to facilitate insertion into and out of muscle, particularly thick muscle.

As shown, the proximal end of needle 30 has the same diameter as the needle shaft. Alternatively, the proximal end of the needle 30 may be flared to create an opening and facilitate entry of the electrode through the target tissue (such as the epimysium and muscle fibers of the diaphragm).

The size of the needle depends on the application and/or site to which the electrode is being directed. For implantation of a temporary intramuscular electrode in the diaphragm, suitable needle sizes range from 28 gauge to 16 gauge. Other applications may require other needle sizes either larger or smaller. The shaft of needle 30 is typically longer than the length of the de-insulated electrode. For example, for use of an embodiment in the diaphragm, the portion of electrode 10 in line with lead 12 may have a length of about 10 mm, while barb 14 may have a length of about 5 mm. In this embodiment, the shaft of needle 30 may be about 20 mm long, and the curved tip 32 may extend about 2.5 mm up from the needle shaft axis. The portion of core 22 extending past electrode 10 to needle 30 is about 20 mm. Electrical lead 12 must be long enough to extend from the implantation site in the diaphragm to the connector 16 outside of the patient, a length of at least about 300 mm.

FIG. 2 shows another embodiment that includes an implantation needle 30 with a straight tip 34. All other elements of the invention are the same as the FIG. 1 embodiment and are labeled accordingly. This straight-tip needle may be used for thinner muscle or for other tissue so that as the needle is inserted into the tissue at a shallow angle, the tip does not emerge from the tissue before a proper distance has been traversed by the needle. Additionally, in other embodiments, the needle may have an alternate shape (such as an intermediate inflection point) to facilitate tissue entry without prematurely emerging from the tissue until an appropriate or sufficient distance has been traversed by the needle.

When implanting the electrode of FIG. 1 or FIG. 2 into a target tissue site such as the diaphragm, the needle 30 is inserted and guided laparoscopically into the abdomen below the diaphragm at the desired implant location. (The appropriate electrode implant locations may be determined using the mapping procedure described by Onders, et. al., "Mapping the phrenic nerve motor point: the key to a successful laparoscopic diaphragm pacing system in the first human series." Surgery 136(4): 819-26, 2004.) Implantation may also occur above the diaphragm using thoracoscopic techniques, or it may also occur above or below the diaphragm using open surgical techniques. The curved distal tip 32 of the needle is passed into the diaphragm, and then guided out (like a sewing needle) at a point preferably at least about 10 mm distal to the entry point. The needle is advanced further distally to pull or embed the electrode 10 into the diaphragm tissue. The heat bonding between core 22 and electrode 10 helps ensure that the electrode will advance into the tissue without sliding back on the lead when encountering tissue resistance. Electrode barb 14 folds back toward the linear axis of the device as the electrode is advanced distally into the tissue, but prevents the electrode from being easily pulled back proximally.

Connector 16 and the proximal end of lead 12 may be tunneled subcutaneously before exiting through the patient's skin via a needle (or trocar) puncture to provide a connection to an external stimulator. After the electrode is in the desired location in the diaphragm, core 22 may be cut between the proximal end of needle 30 and the core's exit point from the diaphragm, and the needle may be removed from the patient.

FIG. 3 shows another embodiment of electrode system that is similar to the embodiments of FIGS. 1 and 2 except that it lacks the implantation needle and has instead a knob 25. All other elements of the device of identical to those of FIGS. 1 and 2 and labeled accordingly. Knob 25 may be formed by melting the distal terminal portion of the core, or it may be formed by any suitable method or formed of any suitable material such that it is firmly bonded to the core 22 or integral with the core 22. This particular embodiment is appropriate for use in conjunction with a surgical instrument for implanting electrodes such as that described in U.S. Pat. No. 5,797,923 of Aiyar and Mortimer. In this particular use of the embodiment of the invention, the knob 25 may be finished flush with the electrode 10 to provide a feature with which the instrument can engage to facilitate ejection of the electrode and lead from the surgical instrument, and in so doing, insert the electrode system into the target site.

Certain forms of diaphragm pacing may be performed for a finite period of time. For example, diaphragm pacing may help wean patients from mechanical ventilation sooner and more easily than could otherwise be weaned. Once diaphragm pacing is no longer needed, removal of the electrode and lead from the patient's diaphragm and abdomen is desired.

To remove electrode 10 from the patient, connector 16 is first cut off the proximal end of lead 12. Since core 22 is bound to connector 16 but is not bound to the insulated portion of lead 12, cutting off the connector allows the proximal ends of core 22 and lead 12 to be moved independently. Helical lead 12 may then be straightened, or unwound from around the core and pulled proximally to dislodge electrode 10 from the tissue. Concurrently, core 22 may be pulled proximally as well, independently of lead 12. The combination of the pulling effects of the lead and the core helps the electrode become dislodged from the tissue despite any encapsulation or fibrosis around the electrode. In addition, the electrode barb 14 may straighten in response to sufficient proximal force to allow the electrode to exit the tissue more easily.

What is claimed is:

1. A method of inserting and removing an electrode in target tissue in a patient for short term or temporary stimulation of the target tissue, the method comprising:
    inserting a tissue-piercing guide into and through the target tissue;
    pulling an electrode connected to a proximal end of the tissue-piercing guide into the target tissue, the electrode being connected to the tissue-piercing guide by a tether extending distally from the electrode;
    extending an electrical lead and the tether proximally from the electrode to an electrical connection location wherein the electrical lead surrounds at least a portion of the tether;
    applying electrical stimulation to the target tissue through the electrode after the step of extending the electrical lead; and
    removing the electrode from the target tissue, the removing step comprising separating the electrical lead and the tether prior to pulling proximally on the electrical lead and pulling proximally on the tether.

2. The method of claim 1 wherein the electrode comprises a barb, the method further comprising pulling the barb into the target tissue.

3. The method of claim 1 further comprising cutting the tether between the electrode and the tissue-piercing guide after the pulling step and removing the tissue-piercing guide from the patient.

4. The method of claim 1 wherein the electrical lead and tether terminate in an electrical connector, the removing step further comprising removing the electrical connector from the electrical lead and tether.

5. A method of inserting and removing an electrode in target tissue in a patient for short term or temporary stimulation of the target tissue, the method comprising:
    inserting an electrode into the target tissue, the electrode being bonded to a tether and electrically connected to an electrical lead;
    extending an electrical lead and the tether proximally from the electrode to an electrical connection location, wherein the electrical lead surrounds at least a portion of the tether;
    applying electrical stimulation to the target tissue through the electrode after the step of extending the electrical lead; and removing the electrode from the target tissue, the removing step comprising separating the electrical lead and the tether prior to pulling proximally on the electrical lead and pulling proximally on the tether.

6. The method of claim 5 wherein the electrical lead and tether terminate in an electrical connector, the removing step further comprising removing the electrical connector from the electrical lead and tether.

* * * * *